United States Patent
Hyun

(10) Patent No.: US 7,621,872 B2
(45) Date of Patent: Nov. 24, 2009

(54) METHOD AND APPARATUS FOR DISPLAYING A COLOR FLOW IMAGE IN AN ULTRASOUND DIAGNOSTIC SYSTEM

(75) Inventor: Dong Gyu Hyun, Gwangju-si (KR)

(73) Assignee: Medison Co., Ltd., Hongchun-gun (KR)

( * ) Notice: Subject to any disclaimer, the term of this patent is extended or adjusted under 35 U.S.C. 154(b) by 278 days.

(21) Appl. No.: 11/473,181

(22) Filed: Jun. 23, 2006

(65) Prior Publication Data

US 2007/0038104 A1 Feb. 15, 2007

(30) Foreign Application Priority Data

Jun. 28, 2005 (KR) ............... 10-2005-0056011

(51) Int. Cl.
*A61B 8/00* (2006.01)
(52) U.S. Cl. ...................... 600/443; 382/182
(58) Field of Classification Search ................ 600/437, 600/443, 453, 463, 468; 604/19, 20, 606, 604/601
See application file for complete search history.

(56) References Cited

U.S. PATENT DOCUMENTS

| | | | |
|---|---|---|---|
| 6,245,017 B1 * | 6/2001 | Hashimoto et al. ........... | 600/447 |
| 2003/0097068 A1 * | 5/2003 | Hossack et al. ............. | 600/443 |
| 2007/0038104 A1 | 2/2007 | Hyun | |

FOREIGN PATENT DOCUMENTS

EP  0797 106 A2  9/1997
EP  0797 106 A3  9/1997

OTHER PUBLICATIONS

U.S. Appl. No. 11/566,851, filed Dec. 5, 2006, Hyun.
U.S. Appl. No. 11/627,200, filed Jan. 25, 2007, Hyun.
U.S. Appl. No. 11/739,431, filed Apr. 24, 2007, Shin.
U.S. Appl. No. 11/476,111, filed Jun. 28, 2006, Hyun.
Mike G. Jones, et al. "Visualization of 4-D Colour and Power Doppler Data." Ultasound in Medicine and Biology, vol. 29, No. 12, Dec. 2003, pp. 1735-1747, XP004482541.
M Teistler, et al. : "Visualization of Echocardiographic Data Using Virtual Scenes". Computers in Cardiology, 1999 Hannover, Germany Sep. 26-29, 1999, Piscataway, NJ, USA. IEEE, US, Sep. 26, 1999, pp. 399-402, XP010367055.

* cited by examiner

*Primary Examiner*—Long V Le
*Assistant Examiner*—Saurel J Selkin
(74) *Attorney, Agent, or Firm*—Oblon, Spivak, McClelland, Maier & Neustadt, L.L.P.

(57) ABSTRACT

The present invention relates to a method and an ultrasound diagnostic system for displaying a 3-dimensional color flow image performing a transparency treatment for a predetermined region. The method of displaying a color flow image, comprises: a) forming a plurality of 2-dimensional color flow images based on ultrasound echo signals; b) sequentially superposing the plurality of 2-dimensional color flow images to form a 3-dimensional color flow image including a plurality of image regions; c) receiving selection information for selecting a desirable image region from the 3-dimensional color flow image; and d) performing a transparency treatment upon the selected region in the 3-dimensional color flow to have a predetermined transparency.

2 Claims, 4 Drawing Sheets

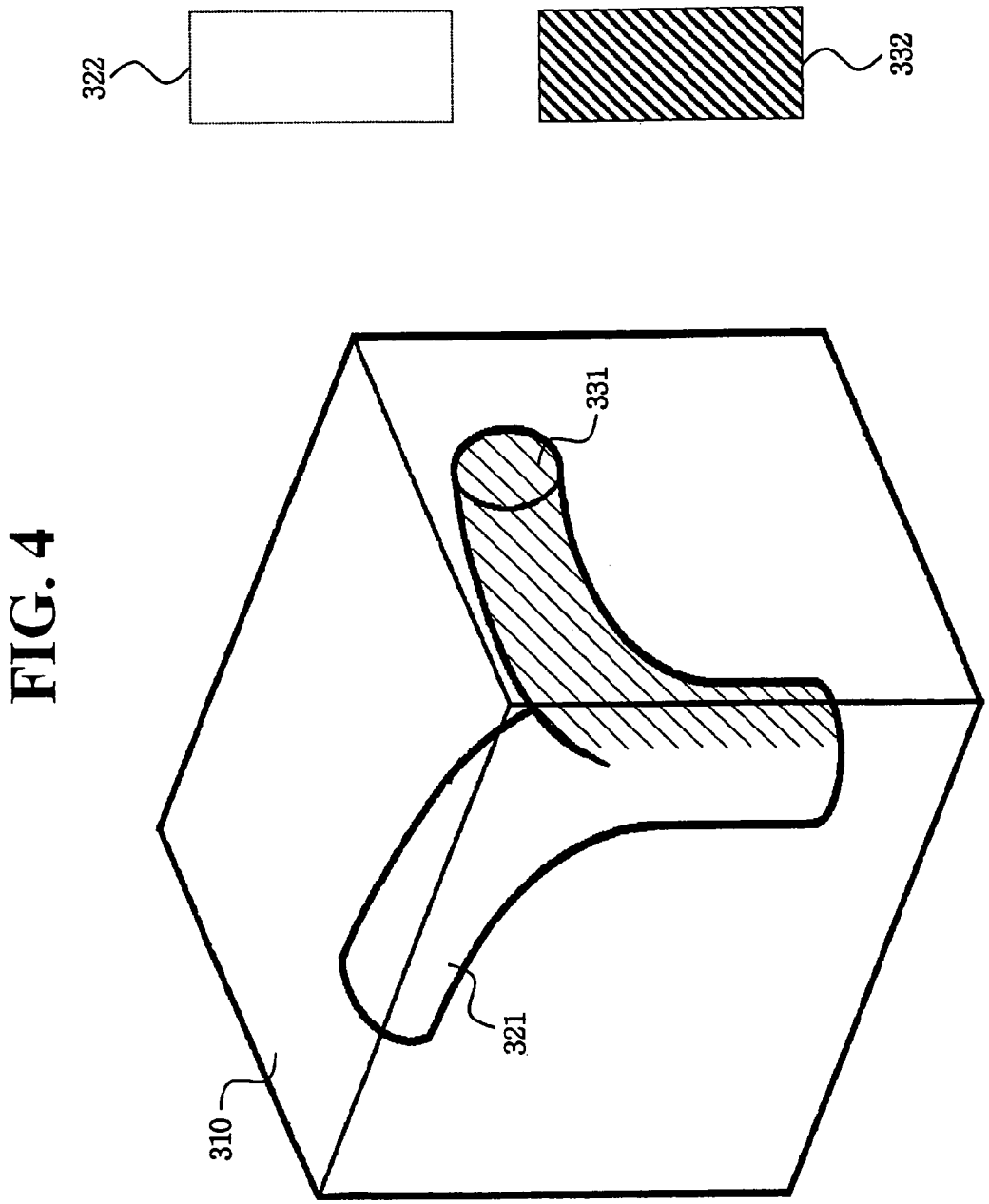

METHOD AND APPARATUS FOR DISPLAYING A COLOR FLOW IMAGE IN AN ULTRASOUND DIAGNOSTIC SYSTEM

FIELD OF THE INVENTION

The present invention generally relates to ultrasound diagnostic systems, and more particularly to an apparatus and method for displaying a color flow image in an ultrasound diagnostic system.

BACKGROUND OF THE INVENTION

Generally, an ultrasound diagnostic system projects ultrasound signals from a surface of a target object toward a desired part within the target object. This is to obtain an ultrasound image of a soft tissue or blood flow by non-invasive means through using information of ultrasound echo signals from the target object. Compared to other medical imaging systems (e.g., X-ray diagnostic system, X-ray CT scanner, MRI and nuclear medicine diagnostic system), the ultrasound diagnostic system is advantageous since it is small in size and fairly inexpensive. Further, the ultrasound diagnostic system is capable of providing real-time display and is highly safe without any dangerous side effects such as exposure to X-rays, etc. Thus, it is extensively utilized for diagnosing the heart, abdomen and urinary organs, as well as being widely applied in the fields of obstetrics, gynecology, etc.

The ultrasound diagnostic system forms ultrasound images of various modes (e.g., B-mode, M-mode, etc.) based on the ultrasound echo signals reflected from the target object. Also, the ultrasound diagnostic system can provide a color flow image, which indicates the velocities of a moving target object and scatters. The ultrasound diagnostic system displays the velocity and direction of blood flowing within a moving object (e.g., heart, blood vessel or the like) with various colors based on the Doppler shift of an ultrasound signal. For example, the conventional ultrasound diagnostic system indicates the blood flowing toward the transducer of the probe with a red color, while indicating the blood flowing backward from the transducer of the probe with a blue color. Furthermore, the conventional diagnostic system indicates a rapidly flowing blood with a light color, while indicating a slowly flowing blood with a dark color.

Since the conventional diagnostic system displays the color Doppler image, which indicates the velocities of the moving target object and the scatters, on a 2-dimensional level, there is a problem in that a person unskilled in the conventional diagnostic system cannot accurately analyze the 2-dimensional color Doppler image.

In order to overcome the above problem, the conventional ultrasound diagnostic system superposes a plurality of 2-dimensional ultrasound images to provide a 3-dimensional color Doppler image. This is so that the above unskilled person can easily examine the target object through the displayed 3-dimensional color Doppler image. However, if the 2-dimensional color Doppler images indicating different blood flows are superposed, then the colors indicating the blood flows are displayed while the images are superposed. Therefore, there is a problem in that the conventional ultrasound diagnostic system cannot provide accurate information of the blood flows.

SUMMARY OF THE INVENTION

The present invention provides an apparatus and a method for performing a transparency treatment for blood flow images with predetermined transparency in the 3-dimensional color flow image to accurately display a target blood flow in an ultrasound diagnostic system.

In accordance with one aspect of the present invention, there is provided a method of displaying a color flow image, comprising: a) forming a plurality of 2-dimensional color flow images based on ultrasound echo signals; b) sequentially superposing the plurality of 2-dimensional color flow images to form a 3-dimensional color flow image including a plurality of image regions; c) receiving selection information for selecting a desirable image region from the 3-dimensional color flow image; and d) performing a transparency treatment upon the selected region in the 3-dimensional color flow image to have a predetermined transparency.

In accordance with another aspect of the present invention, there is provided an apparatus for displaying a color flow image in an ultrasound diagnostic system, comprising: an image forming unit for forming a plurality of 2-dimensional color flow images based on ultrasound echo signals and sequentially superposing the plurality of 2-dimensional color flow images to form a 3-dimensional color flow image including a plurality of image regions; a receiving unit for receiving selection information to select a desirable image region from the 3-dimensional color flow image; and a transparentizing unit for performing a transparency treatment upon the selected region in the 3-dimensional color flow image.

BRIEF DESCRIPTION OF THE DRAWINGS

The above and other objects and features of the present invention will become apparent from the following description of preferred embodiments given in conjunction with the accompanying drawings, in which:

FIG. 4 is a diagram showing a 3-dimensional color flow image in which a selected blood flow image is transparentized.

DETAILED DESCRIPTION OF THE PRESENT INVENTION

Figure 1:
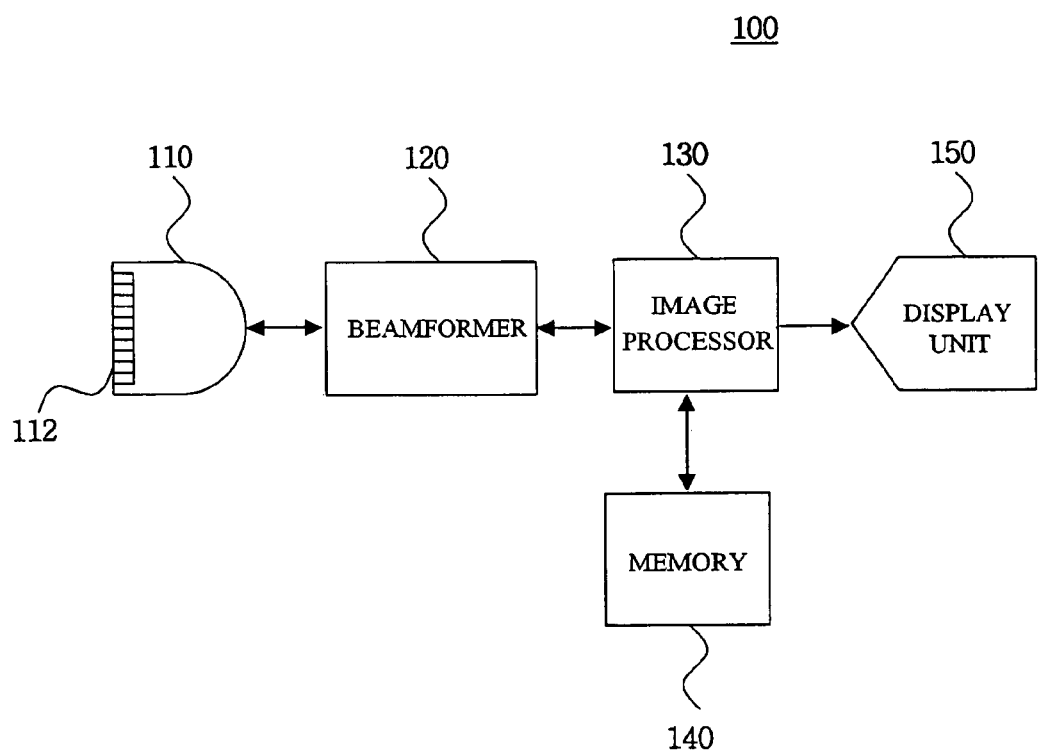
FIG. 1 is a block diagram showing an ultrasound diagnostic system constructed in accordance with the preferred embodiment of the present invention.

FIG. 1 is a block diagram showing an ultrasound diagnostic system 100, which is constructed in accordance with the preferred embodiment of the present invention. As shown in FIG. 1, the ultrasound diagnostic system 100 includes a probe 110, a beam former 120, an image processor 130, a memory 140 and a display unit 150.

The probe 110 includes a 1-dimensional or 2-dimensional array transducer 112. The transmit signals, which are appropriately delayed to form a focused ultrasound beam in the beam former 120, are transmitted to the array transducer 112 and the focused ultrasound beam is transmitted along a scan line of a target object (not shown). The probe 110 receives ultrasound echo signals reflected from the target object and converts the ultrasound echo signals into electric signals (hereinafter referred to as reception signals). The reception signals are transmitted into the beam former 120.

The beam former 120 controls the delay of transmit signals to be transmitted to the array transducer 112 in the probe 110 such that the ultrasound signals outputted from the array transducer 112 are focused on a focal point. Further, the beam former 120 focuses the reception signals received at the array transducer 112 included in the probe 110 in consideration of the delays with which the ultrasound echo signals arrived at each transducer.

The image processor 130 sequentially superposes a plurality of 2-dimensional color flow images, which are formed based on the reception signals outputted from the beam former 120, to form a 3-dimensional color flow image containing blood flow images. The 3-dimensional color flow image includes a plurality of image regions and each region is differently colored. The image processor 130 performs a transparency treatment for a blood flow image region selected by a user to have a predetermined transparency. The 3-dimensional color flow image, which is processed in the image processor 130, may be stored in the memory 140 or displayed on the display unit 150 according to the selection of the user.

Figure 2:
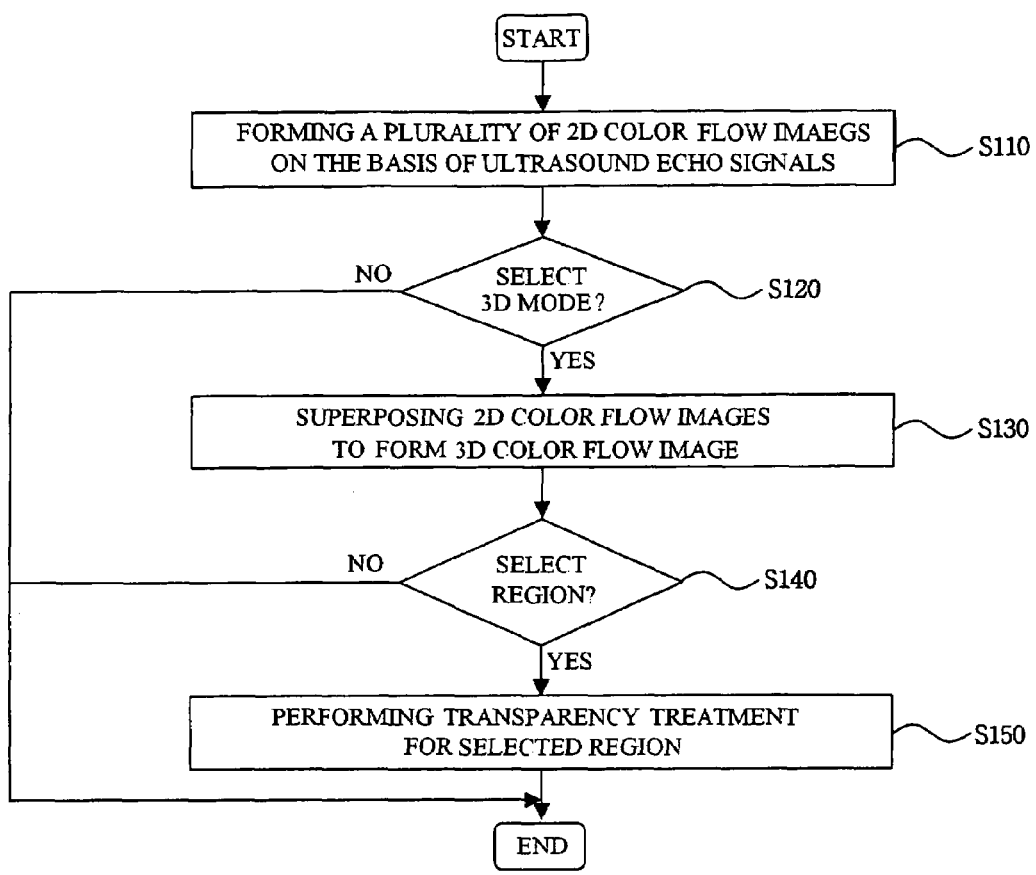
FIG. 2 is a flow chart showing an operation of the image processor constructed in accordance with the present invention.
Figure 3:
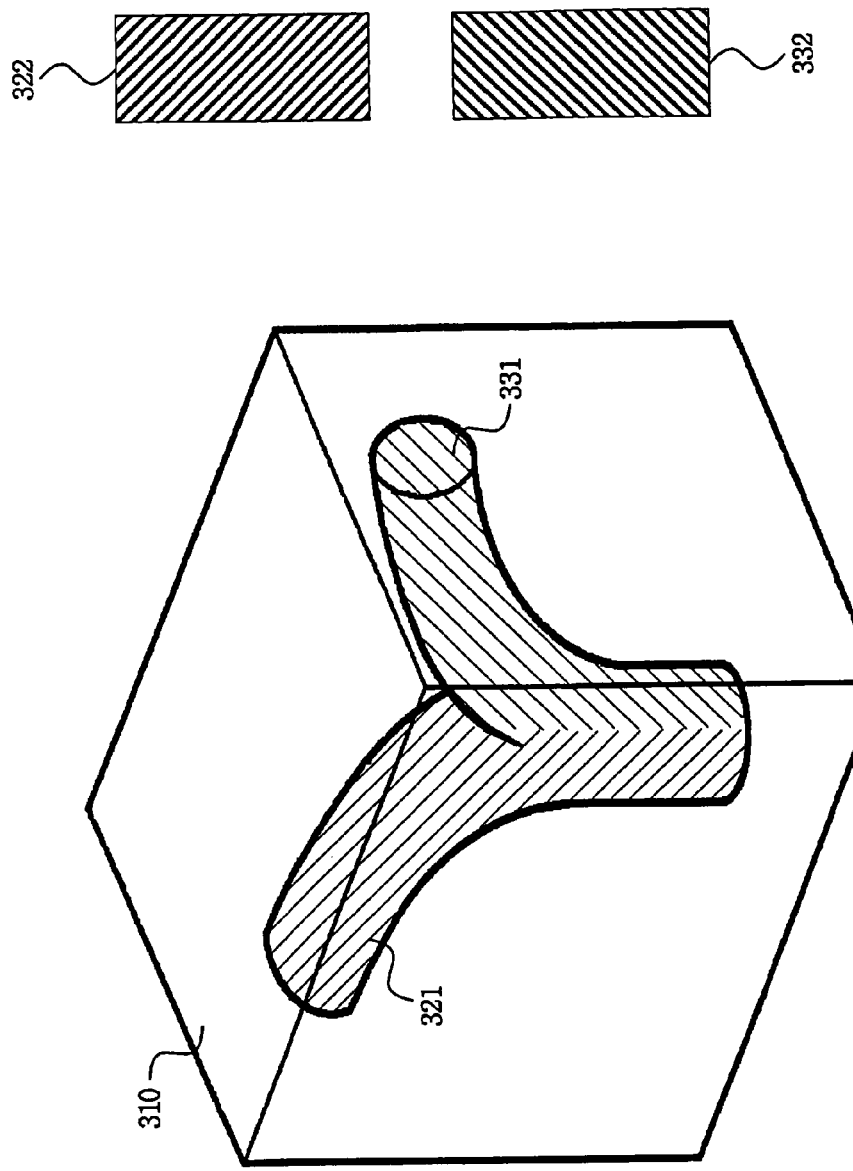
FIG. 3 is a diagram showing a 3-dimensional color flow image formed in accordance with the present invention.

Hereinafter, the operation of the image processor will be described in detail in view of FIGS. 2 to 4. FIG. 2 is a flow chart showing the operation of the image processor, which is constructed in accordance with the present invention. As shown in FIG. 2, the image processor 130 forms the plurality of 2-dimensional color Doppler image based on the focused reception signals outputted from the beam former 120 at step S110. The reception signals include color information of the target object.

The image processor 130 checks whether a 3D mode is selected at step S120. If it is determined that the 3D mode is selected at step S120, then the image processor 130 sequentially superposes the plurality of 2-dimensional color flow images so as to form the 3-dimensioanl color flow image at step S130. The 3-dimensional color ultrasound image 310 includes a plurality of image regions and each region is differently colored. The 3-dimensional color ultrasound image 310 and color maps 322 and 332 corresponding to blood flow images 321 and 331, which are examples formed in the image processor 130, are shown in FIG. 3.

Subsequently, the image processor 130 checks whether a region, which is processed with transparency, is selected based on selection information inputted from the user at step S140. The selected region may correspond to a region, which the user does not wish to observe. In such a case, the selection of the region is carried out by selecting one of the color maps 322 and 332 or one of the colors within the color maps 322 and 332.

If it is determined that the region to be processed with the transparency is selected at step S150, then the image processor 130 performs the transparency treatment for a color of a blood flow in the selected region so as to have a predetermined transparency at step S150. For example, if the color map 322 corresponding to the blood flow image 130 is selected as a region to be transparentized, then the image processor 130 assigns a transparent color having the predetermined transparency to the color indicating the blood flow image 321 and color map 322. Consequently, the color indicating the blood flow image 321 and color map 322 are transparentized, as shown in FIG. 4.

According to the preferred embodiment of the present invention, the region selected by the user is transparentized as a region that is not to be observed. However, the regions, which are not selected by the user, may be set as regions that are not to be observed. This is so that the transparency treatment may be performed to the regions with the exception of the selected regions in accordance with another embodiment of the present invention.

As the transparency treatment is selectively carried out for colors corresponding to the blood flow images that are superposed, the blood flow image to be observed can be separately displayed. This is so that the user can accurately examine the blood flow image that the user wishes to observe.

While the present invention has been described and illustrated with respect to a preferred embodiment of the invention, it will be apparent to those skilled in the art that variations and modifications are possible without deviating from the broad principles and teachings of the present invention which should be limited solely by the scope of the claims appended hereto.

What is claimed is:

1. A method of displaying a color flow image in an ultrasound diagnostic system, comprising the steps of:
    a) forming a plurality of 2-dimensional color flow images based on ultrasound echo signals;
    b) sequentially superposing the plurality of 2-dimensional color flow images to form a 3-dimensional color flow image including a plurality of image regions, and forming a plurality of color maps corresponding to the 3-dimensional color flow image, each of the said plurality of color maps having colors associated therewith;
    c) receiving selection information from a user for selecting one of the color maps or one of colors in the color maps; and
    d) performing a transparency treatment upon an image region corresponding to the selected color map or color in the 3-dimensional color flow image to have a predetermined transparency.

2. An apparatus for displaying a color flow image in an ultrasound diagnostic system, comprising:
    an image forming unit for forming a plurality of 2-dimensional color flow images based on ultrasound echo signals and sequentially superposing the plurality of 2-dimensional color flow images to form a 3-dimensional color flow image including a plurality of image regions, the image forming unit further forming color maps corresponding to the 3-dimensional color flow image, each of the said plurality of color maps having colors associated therewith;
    a receiving unit for receiving selection information from a user to select one of the color maps or one of colors in the color maps; and
    a transparentizing unit for performing a transparency treatment upon an image region corresponding to the selected color map or color in the 3-dimensional color flow image.

* * * * *